United States Patent [19]
Olson et al.

[11] Patent Number: 5,811,441
[45] Date of Patent: Sep. 22, 1998

[54] ISOXAZOLINE FIBRINOGEN RECEPTOR ANTAGONISTS

[75] Inventors: Richard Eric Olson, Wilmington, Del.; John Wityak, West Grove, Pa.

[73] Assignee: The DuPont Merck Pharmaceutical Company, Wilmington, Del.

[21] Appl. No.: 922,488

[22] Filed: Sep. 3, 1997

Related U.S. Application Data

[63] Continuation of Ser. No. 791,095, Jan. 27, 1997, abandoned, which is a continuation of Ser. No. 586,940, Jan. 11, 1996, abandoned, which is a continuation of Ser. No. 449,597, May 24, 1995, abandoned.

[51] Int. Cl.[6] ............... A61K 31/415; A61K 31/535; C07D 413/12; C07D 413/14
[52] U.S. Cl. ............. 514/380; 548/243; 544/137; 514/236.8
[58] Field of Search ............... 514/236.8; 544/380, 544/137; 548/243

[56] References Cited

U.S. PATENT DOCUMENTS

| 5,039,805 | 8/1991 | Al.Ig et al. . |
| 5,059,614 | 10/1991 | Lepage et al. ............ 548/243 |
| 5,227,490 | 7/1993 | Hartman et al. . |
| 5,276,049 | 1/1994 | Himmelsbach et al. . |
| 5,281,585 | 1/1994 | Himmelsbach et al. . |
| 5,334,596 | 8/1994 | Hartman et al. . |

FOREIGN PATENT DOCUMENTS

| 2008311 | 7/1990 | Canada . |
| 2061661 | 9/1992 | Canada . |
| 2074685 | 1/1993 | Canada . |
| 2075590 | 9/1993 | Canada . |
| 2093770 | 10/1993 | Canada . |
| 2094773 | 10/1993 | Canada . |
| 2094964 | 10/1993 | Canada . |
| 2101179 | 1/1994 | Canada . |
| 2105934 | 3/1994 | Canada . |
| 2144762 | 4/1994 | Canada . |
| 2114178 | 7/1994 | Canada . |
| 2116068 | 8/1994 | Canada . |
| 2174838 | 6/1995 | Canada . |
| 381033 | 8/1990 | European Pat. Off. . |
| 445796 | 9/1991 | European Pat. Off. . |
| 478328 | 4/1992 | European Pat. Off. . |
| 478362 | 4/1992 | European Pat. Off. . |
| 478363 | 4/1992 | European Pat. Off. . |
| 512829 | 11/1992 | European Pat. Off. . |
| 512831 | 11/1992 | European Pat. Off. . |
| 513810 | 11/1992 | European Pat. Off. . |
| 525629 | 2/1993 | European Pat. Off. . |
| 566919 | 10/1993 | European Pat. Off. . |
| 567968 | 11/1993 | European Pat. Off. . |
| 580008 | 1/1994 | European Pat. Off. . |
| 9307867 | 4/1993 | WIPO . |
| 9316697 | 9/1993 | WIPO . |
| 9318057 | 9/1993 | WIPO . |
| 9402472 | 2/1994 | WIPO . |
| 9408577 | 4/1994 | WIPO . |
| 9408962 | 4/1994 | WIPO . |
| 9412181 | 6/1994 | WIPO . |
| 9418981 | 9/1994 | WIPO . |
| 9504531 | 2/1995 | WIPO . |
| 9506038 | 2/1995 | WIPO . |
| 9514682 | 6/1995 | WIPO . |
| 9514683 | 6/1995 | WIPO . |

OTHER PUBLICATIONS

Phillips et al., *Cell* (1991) 65, pp. 359–362.
Hartman et al., *J. Med. Chem.* (1992) 35, pp. 4640–4642.
Al.ig et al., *J. Med. Chem.* (1992) 35, pp. 4393–4407.
Askew et al., *Bioorg. Med. Chem. Lett.* (1995) 5, p. 475.
Alig et al. *J. Med. Chem.* (1992) 35: 4393–4407.
Askew et al. *Bioorg. Med. Chem. Lett.* (1995) 5: 475.

*Primary Examiner*—Patricia L. Morris

[57] ABSTRACT

This invention relates to improved isoxazoline compounds including, but not limited to $N^2$-(3,5-dimethylisoxazole-4-sulfonyl)-$N^3$-[3-(4-amidinophenyl)isoxazolin-5(R)-ylacetyl]-(S)-2,3-diaminopropionic acid, which are useful as antagonists of the platelet glycoprotein IIb/IIIa fibrinogen receptor complex, to pharmaceutical compositions containing such compounds, and to methods of using these compounds, alone or in combination with other therapeutic agents, for the inhibition of platelet aggregation, as thrombolytics, and/or for the treatment of thromboembolic disorders.

20 Claims, No Drawings

ISOXAZOLINE FIBRINOGEN RECEPTOR ANTAGONISTS

This is a continuation, of application Ser. No. 08/791,095 filed on Jan. 27, 1997, now abandoned which, in turn, is a continuation of Ser. No. 08/586,940 filed Jan. 11, 1996, now abandoned which in turn is a continuation of Ser. No. 08/449,597 filed May 24, 1995, now abandoned.

FIELD OF THE INVENTION

This invention relates to improved isoxazolines which are useful as antagonists of the platelet glycoprotein IIb/IIIa fibrinogen receptor complex, to pharmaceutical compositions containing such compounds, and to methods of using these compounds, alone or in combination with other therapeutic agents, for the inhibition of platelet aggregation, as thrombolytics, and/or for the treatment of thromboembolic disorders.

BACKGROUND OF THE INVENTION

Hemostasis is the normal physiological process in which bleeding from an injured blood vessel is arrested. It is a dynamic and complex process in which platelets play a key role. Within seconds of vessel injury, resting platelets become activated and are bound to the exposed matrix of the injured area by a phenomenon called platelet adhesion. Activated platelets also bind to each other in a process called platelet aggregation to form a platelet plug. The platelet plug can stop bleeding quickly, but it must be reinforced by fibrin for long-term effectiveness, until the vessel injury can be permanently repaired.

Thrombosis may be regarded as the pathological condition wherein improper activity of the hemostatic mechanism results in intravascular thrombus formation. Activation of platelets and the resulting platelet aggregation and platelet factor secretion has been associated with a variety of pathophysiological conditions including cardiovascular and cerebrovascular thromboembolic disorders, for example, the thromboembolic disorders associated with unstable angina, myocardial infarction, transient ischemic attack, stroke, atherosclerosis and diabetes. The contribution of platelets to these disease processes stems from their ability to form aggregates, or platelet thrombi, especially in the arterial wall following injury.

Platelets are activated by a wide variety of agonists resulting in platelet shape change, secretion of granular contents and aggregation. Aggregation of platelets serves to further focus clot formation by concentrating activated clotting factors at the site of injury. Several endogenous agonists including adenosine diphosphate (ADP), serotonin, arachidonic acid, thrombin, and collagen, have been identified. Because of the involvement of several endogenous agonists in activating platelet function and aggregation, an inhibitor which acts against all agonists would represent a more efficacious antiplatelet agent than currently available antiplatelet drugs, which are agonist-specific.

Current antiplatelet drugs are effective against only one type of agonist; these include aspirin, which acts against arachidonic acid; ticlopidine, which acts against ADP; thromboxane $A_2$ synthetase inhibitors or receptor antagonists, which act against thromboxane $A_2$; and hirudin, which acts against thrombin.

Recently, a common pathway for all known agonists has been identified, namely platelet glycoprotein IIb/IIIa complex (GPIIb/IIIa), which is the membrane protein mediating platelet aggregation. A recent review of GPIIb/IIIa is provided by Phillips et al. *Cell* (1991) 65: 359–362. The development of a GPIIb/IIIa antagonist represents a promising new approach for antiplatelet therapy.

GPIIb/IIIa does not bind soluble proteins on unstimulated platelets, but GPIIb/IIIa in activated platelets is known to bind four soluble adhesive proteins, namely fibrinogen, von Willebrand factor, fibronectin, and vitronectin. The binding of fibrinogen and von Willebrand factor to GPIIb/IIIa causes platelets to aggregate. The binding of fibrinogen is mediated in part by the Arg-Gly-Asp (RGD) recognition sequence which is common to the adhesive proteins that bind GPIIb/IIIa.

In addition to GPIIb/IIIa, increasing numbers of other cell surface receptors have been identified which bind to extracellular matrix ligands or other cell adhesion ligands thereby mediating cell—cell and cell-matrix adhesion processes. These receptors belong to a gene superfamily called integrins and are composed of heterodimeric transmembrane glycoproteins containing $\alpha$- and $\beta$-subunits. Integrin subfamilies contain a common $\beta$-subunit combined with different $\alpha$-subunits to form adhesion receptors with unique specificity. The genes for eight distinct $\beta$-subunits have been cloned and sequenced to date.

Two members of the $\beta 1$ subfamily, $\alpha 4/\beta 1$ and $\alpha 5/\beta 1$ have been implicated in various inflammatory processes. Antibodies to $\alpha 4$ prevent adhesion of lymphocytes to synovial endothelial cells in vitro, a process which may be of importance in rheumatoid arthritis (VanDinther-Janssen et al., J. Immunol., 1991, 147:4207). Additional studies with monoclonal anti-$\alpha 4$ antibodies provide evidence that $\alpha 4/\beta 1$ may additionally have a role in allergy, asthma, and autoimmune disorders (Walsh et al., J. Immunol., 1991, 146:3419; Bochner et al., J. Exp. Med., 1991 173:1553; Yednock et al., Nature, 1992, 356:63). Anti-$\alpha 4$ antibodies also block the migration of leukocytes to the site of inflammation (Issedutz et al., J. Immunol., 1991, 147:4178).

The $\alpha_v/\beta_3$ heterodimer, commonly referred to as the vitronectin receptor, is another member of the $\beta_3$ integrin subfamily and has been described in platelets, endothelial cells, melanoma, smooth muscle cells and on the surface of osteoclasts (Horton and Davies, J. Bone Min. Res. 1989, 4:803–808; Davies et al., J. Cell. Biol. 1989, 109:1817–1826; Horton, Int. J. Exp. Pathol., 1990, 71:741–759). Like GPIIb/IIIa, the vitronectin receptor binds a variety of RGD-containing adhesive proteins such as vitronectin, fibronectin, VWF, fibrinogen, osteopontin, bone sialo protein II and thrombosponden in a manner mediated by the RGD sequence. Possible roles for $\alpha_v/\beta_3$ in angiogenesis, tumor progression, and neovascularization have been proposed (Brooks et al., Science, 1994, 264:569–571). A key event in bone resorption is the adhesion of osteoclasts to the matrix of bone. Studies with monoclonal antibodies have implicated the $\alpha_v/\beta_3$ receptor in this process and suggest that a selective $\alpha_v/\beta_3$ antagonist would have utility in blocking bone resorption (Horton et al., J. Bone Miner. Res., 1993, 8:239–247; Helfrich et al., J. Bone Miner. Res., 1992, 7:335–343).

Several RGD-peptidomimetic compounds have been reported which block fibrinogen binding and prevent the formation of platelet thrombi.

European Patent Application Publication Number 478, 363 relates to compounds having the general formula:

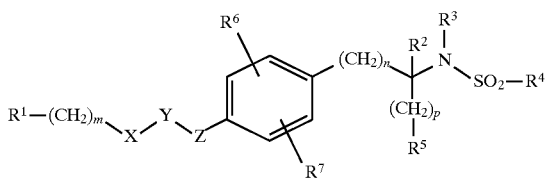

European Patent Application Publication Number 478, 328 relates to compounds having the general formula:

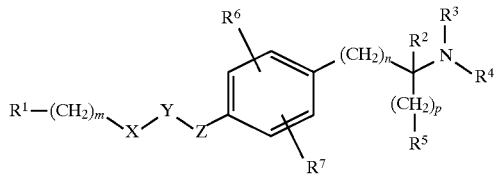

European Patent Application Publication Number 525, 629 (corresponds to Canadian Patent Application Publication Number 2,074,685) discloses compounds having the general formula:

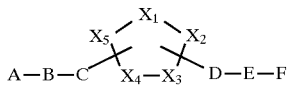

PCT Patent Application 93/07867 relates to compounds having the general formula:

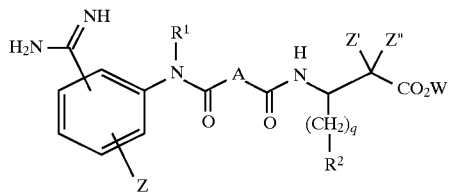

European Patent Application Publication Number 512, 831 relates to compounds having the general formula:

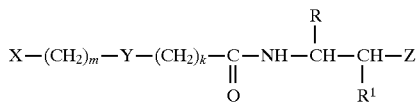

None of the above references teaches or suggests the compounds of the present invention which are described in detail below.

Copending, commonly assigned U.S. patent application Ser. No. 08/337,920, filed Nov. 10, 1994, relates to compounds having the general formula:

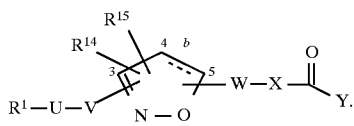

The compounds of the present invention have unexpected and advantageous pharmaceutical properties.

SUMMARY OF THE INVENTION

The present invention provides novel nonpeptide compounds which bind to integrin receptors thereby altering cell-matrix and cell—cell adhesion processes. The compounds of the present invention are useful for the treatment of thrombosis, inflammation, bone degradation, tumors, metastases, thrombosis, and cell aggregation-related conditions in a mammal.

One aspect of this invention provides novel compounds of Formula I (described below) which are useful as antagonists of the platelet glycoprotein IIb/IIIa complex. The compounds of the present invention inhibit the binding of fibrinogen to platelet glycoprotein IIb/IIIa complex and inhibit the aggregation of platelets. The present invention also includes pharmaceutical compositions containing such compounds of Formula I, and methods of using such compounds for the inhibition of platelet aggregation, as thrombolytics, and/or for the treatment of thromboembolic disorders.

The present invention also includes methods of treating cardiovascular disease, thrombosis or harmful platelet aggregation, reocclusion following thrombolysis, reperfusion injury, or restenosis by administering a compound of Formula I alone or in combination with one or more additional therapeutic agents selected from: anti-coagulants such as warfarin or heparin; anti-platelet agents such as aspirin, piroxicam or ticlopidine; thrombin inhibitors; or thrombolytic agents such as tissue plasminogen activator, anistreplase, urokinase or streptokinase; or combinations thereof.

The present invention also provides novel compounds, pharmaceutical compositions and methods which may be used in the treatment or prevention of diseases which involve cell adhesion processes, including, but not limited to, rheumatoid arthritis, asthma, allergies, adult respiratory distress syndrome, graft versus host disease, organ transplantation, septic shock, psoriasis, eczema, contact dermatitis, osteoporosis, osteoarthritis, atherosclerosis, metastasis, wound healing, diabetic retinopathy, inflammatory bowel disease and other autoimmune diseases. Also included in the present invention are pharmaceutical kits comprising one or more containers containing pharmaceutical dosage units comprising a compound of Formula I, for the treatment of cell adhesion related disorders, including but not limited to thromboembolic disorders.

DETAILED DESCRIPTION OF THE INVENTION

The present invention provides novel nonpeptide compounds of Formula I (described below) which bind to integrin receptors thereby altering cell-matrix and cell—cell adhesion processes. The compounds of the present invention are useful for the treatment of thrombosis, inflammation, bone degradation, tumors, metastases, and cell aggregation-related conditions in a mammal.

One aspect of this invention provides compounds of Formula I (described below) which are useful as antagonists of the platelet glycoprotein IIb/IIIa complex. The compounds of the present invention inhibit the binding of fibrinogen to the platelet glycoprotein IIb/IIIa complex and inhibit the aggregation of platelets. The present invention also includes pharmaceutical compositions containing such compounds of Formula I, and methods of using such compounds for the inhibition of platelet aggregation, as thrombolytics, and/or for the treatment of thromboembolic disorders.

The present invention comprises compounds of the Formula I:

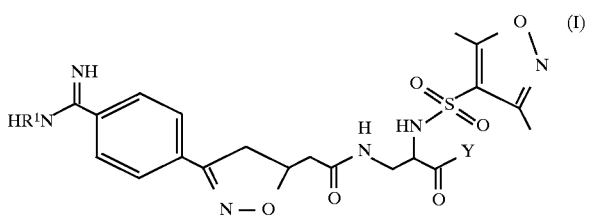

including zwitterion and pharmaceutically acceptable salt forms thereof, and stereoisomeric forms and mixtures of stereoisomeric forms thereof, and prodrug forms thereof wherein:

$R^1$ is hydrogen, $(C_1-C_6)$alkoxycarbonyl, $(C_3-C_7)$ cycloalkoxycarbonyl or aryloxycarbonyl;

Y is selected from the group consisting of:
hydroxy,
$C_1-C_{10}$ alkyloxy,
$C_3-C_{11}$ cycloalkyloxy, aryl $C_1-C_6$ alkyloxy,
$C_1-C_6$ alkylcarbonyloxy $C_1-C_4$ alkyloxy,
$C_1-C_6$ alkyloxycarbonyloxy $C_1-C_4$ alkyloxy,
$C_3-C_7$ cycloalkylcarbonyloxy $C_1-C_4$ alkyloxy,
$C_3-C_7$ cycloalkyloxycarbonyloxy $C_1-C_4$ alkyloxy,
$C_8-C_{14}$ arylcarbonyloxy $C_1-C_4$ alkyloxy,
$C_1-C_6$ alkyloxy $C_1-C_6$ alkylcarbonyloxy $C_1-C_4$ alkyloxy,
[5-$(C_1-C_6)$alkyl-1,3-dioxa-cyclopenten-2-one-4-yl]methyloxy,
(5-aryl-1,3-dioxa-cyclopenten-2-one-4-yl)methyloxy,
$(C_1-C_4$ alkyl$)_2$N-$(C_1-C_{10})$alkyloxy, and morpholinoethoxy;

wherein aryl is phenyl or naphthyl optionally substituted with 1–3 substituents independently selected from: methyl, trifluoromethyl, methoxy, amino, dimethylamino, F, Cl, Br and I.

Preferred compounds of the present invention are compounds of the Formula I wherein:

$R^1$ is H, methoxycarbonyl, ethoxycarbonyl or benzyloxycarbonyl.

More preferred are compounds of the Formula I, including zwitterion and pharmaceutically acceptable salt forms thereof, and stereoisomeric forms and mixtures of stereoisomeric forms thereof, and prodrug forms thereof, wherein:

$R^1$ is H; and

Y is selected from the group consisting of:
hydroxy, methoxy, ethoxy, isopropoxy, n-propoxy, n-butoxy, tert-butoxy, iso-butoxy, sec-butoxy,
methylcarbonyloxymethoxy,
ethylcarbonyloxymethoxy,
t-butylcarbonyloxymethoxy,
cyclohexylcarbonyloxymethoxy,
1-(methylcarbonyloxy)ethoxy,
1-(ethylcarbonyloxy)ethoxy,
1-(t-butylcarbonyloxy)ethoxy,
1-(cyclohexylcarbonyloxy)ethoxy,
i-propyloxycarbonyloxymethoxy,
cyclohexyloxycarbonyloxymethoxy,
t-butyloxycarbonyloxymethoxy,
1-(i-propyloxycarbonyloxy)ethoxy,
1-(cyclohexyloxycarbonyloxy)ethoxy,
1-(t-butyloxycarbonyloxy)ethoxy,
dimethylaminoethoxy, diethylaminoethoxy,
(5-methyl-1,3-dioxacyclopenten-2-on-4-yl)methoxy,
(5-(t-butyl)-1,3-dioxacyclopenten-2-on-4-yl)methoxy,
(1,3-dioxa-5-phenyl-cyclopenten-2-on-4-yl)methoxy, and
1-(2-(2-methoxypropyl)carbonyloxy)ethoxy-.

Most preferred compounds of the present invention are compounds, including zwitterion and pharmaceutically acceptable salt forms thereof, and the methyl and ethyl ester forms thereof, selected from:

$N^2$-(3,5-Dimethylisoxazole-4-sulfonyl)-$N^3$-[3-(4-amidinophenyl)isoxazolin-5(R)-ylacetyl]-(S)-2,3-diaminopropionic Acid;

$N^2$-(3,5-Dimethylisoxazole-4-sulfonyl)-$N^3$-[3-(4-amidinophenyl)isoxazolin-5(S)-ylacetyl]-(S)-2,3-diaminopropionic Acid;

$N^2$-(3,5-Dimethylisoxazole-4-sulfonyl)-$N^3$-[3-(4-amidinophenyl)isoxazolin-5(R)-ylacetyl]-(R)-2,3-diaminopropionic Acid;

$N^2$-(3,5-Dimethylisoxazole-4-sulfonyl)-$N^3$-[3-(4-amidinophenyl)isoxazolin-5(S)-ylacetyl]-(R)-2,3-diaminopropionic Acid.

Preferred compounds of the present invention are selected from:

$N^2$-(3,5-Dimethylisoxazole-4-sulfonyl)-$N^3$-[3-(4-amidinophenyl)isoxazolin-5(R)-ylacetyl]-(S)-2,3-diaminopropionic Acid;

$N^2$-(3,5-Dimethylisoxazole-4-sulfonyl)-$N^3$-[3-(4-amidinophenyl)isoxazolin-5(R)-ylacetyl]-(S)-2,3-diaminopropionic Acid TFA Salt;

$N^2$-(3,5-Dimethylisoxazole-4-sulfonyl-$N^3$[3-(4-amidinophenyl)isoxazolin-5(R)-ylacetyl]-(S)-2,3-diaminopropionic Acid Methanesulfonate Salt;

$N^2$-(3,5-Dimethylisoxazole-4-sulfonyl-$N^3$[3-(4-amidinophenyl)isoxazolin-5(R)-ylacetyl]-(S)-2,3-diaminopropionic Acid Hydrochloride Salt.

In the present invention it has been discovered that the compounds of Formula I above are useful as inhibitors of cell-matrix and cell—cell adhesion processes. The present invention includes novel compounds of Formula I and methods for using such compounds for the prevention or treatment of diseases resulting from abnormal cell adhesion to the extracellular matrix which comprises administering to a host in need of such treatment a therapeutically effective amount of such compound of Formula I.

In the present invention it has also been discovered that the compounds of Formula I above are useful as inhibitors of glycoprotein IIb/IIIa (GPIIb/IIIa). The compounds of the present invention inhibit the activation and aggregation of platelets induced by all known endogenous platelet agonists.

The present invention also provides pharmaceutical compositions comprising a compound of Formula I and a pharmaceutically acceptable carrier.

The compounds of Formula I of the present invention are useful for the treatment (including prevention) of thromboembolic disorders. The term "thromboembolic disorders" as used herein includes conditions involving platelet activation and aggregation, such as arterial or venous cardiovascular or cerebrovascular thromboembolic disorders, including, for example, thrombosis, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, myocardial infarction, cerebral embolism, kidney embolisms, pulmonary embolisms, or such disorders associated with diabetes, comprising administering to a mammal in need of such treatment a therapeutically effective amount of a compound of Formula I described above.

The compounds of Formula I of the present invention may be useful for the treatment or prevention of other diseases which involve cell adhesion processes, including, but not limited to, infammation, bone degradation, rheumatoid arthritis, asthma, allergies, adult respiratory distress syndrome, graft versus host disease, organ transplantation rejection, septic shock, psoriasis, eczema, contact dermatitis, osteoporosis, osteoarthritis, atherosclerosis, tumors, metastasis, diabetic retinopathy, inflammatory bowel disease and other autoimmune diseases. The compounds of Formula I of the present invention may also be useful for wound healing.

The compounds of the present invention are useful for inhibiting the binding of fibrinogen to blood platelets, inhibiting aggregation of blood platelets, treating thrombus formation or embolus formation, or preventing thrombus or embolus formation in a mammal. The compounds of the invention may be used as a medicament for blocking fibrinogen from acting at its receptor site in a mammal.

Compounds of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption, and where the aggregated platelets may form thrombi and thromboemboli. The compounds of the present invention may be administered to these surgical patients to prevent the formation of thrombi and thromboemboli.

Extracorporeal circulation is routinely used during cardiovascular surgery in order to oxygenate blood. Platelets adhere to surfaces of the extracorporeal circuit. Adhesion is dependent on the interaction between GPIIb/IIIa on the platelet membranes and fibrinogen adsorbed to the surface of the extracorporeal circuit. Platelets released from artificial surfaces show impaired homeostatic function. The compounds of the invention may be administered to prevent such ex vivo adhesion.

The compounds of the present invention may be used for other ex vivo applications to prevent cellular adhesion in biological samples.

Other applications of these compounds include prevention of platelet thrombosis, thromboembolism, and reocclusion during and after thrombolytic therapy and prevention of platelet thrombosis, thromboembolism and reocclusion after angioplasty of coronary and other arteries and after coronary artery bypass procedures. The compounds of the present invention may also be used to prevent myocardial infarction. The compounds of the present invention are useful as thrombolytics for the treatment of thromboembolic disorders.

The compounds of the present invention can also be administered in combination with one or more additional therapeutic agents select from: anti-coagulant or coagulation inhibitory agents, such as heparin or warfarin; anti-platelet or platelet inhibitory agents, such as aspirin, piroxicam, or ticlopidine; thrombin inhibitors such as hirudin or argatroban; or thrombolytic or fibrinolytic agents, such as plasminogen activators, anistreplase, urokinase, or streptokinase.

The compounds of Formula I of the present invention can be administered in combination with one or more of the foregoing additional therapeutic agents, thereby to reduce the doses of each drug required to achieve the desired therapeutic effect. Thus, the combination treatment of the present invention permits the use of lower doses of each component, with reduced adverse, toxic effects of each component. A lower dosage minimizes the potential of side effects of the compounds, thereby providing an increased margin of safety relative to the margin of safety for each component when used as a single agent. Such combination therapies may be employed to achieve synergistic or additive therapeutic effects for the treatment of thromboembolic disorders.

By "therapeutically effective amount" it is meant an amount of a compound of Formula I that when administered alone or in combination with an additional therapeutic agent to a cell or mammal is effective to prevent or ameliorate the thromboembolic disease condition or the progression of the disease.

By "administered in combination" or "combination therapy" it is meant that the compound of Formula I and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The term "anti-coagulant agents" (or coagulation inhibitory agents), as used herein, denotes agents that inhibit blood coagulation. Such agents include warfarin (available as Coumadin™) and heparin.

The term "anti-platelet agents" (or platelet inhibitory agents), as used herein, denotes agents that inhibit platelet function such as by inhibiting the aggregation, adhesion or granular secretion of platelets. Such agents include the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam. Piroxicam is commercially available from Pfizer Inc. (New York, N.Y.), as Feldane™. Other suitable anti-platelet agents include ticlopidine, including pharmaceutically acceptable salts or prodrugs thereof. Ticlopidine is also a preferred compound since it is known to be gentle on the gastro-intestinal tract in use. Still other suitable platelet inhibitory agents include thromboxane-A2-receptor antagonists and thromboxane-A2-synthetase inhibitors, as well as pharmaceutically acceptable salts or prodrugs thereof.

The phrase "thrombin inhibitors" (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. Such inhibitors include boroarginine derivatives and boropeptides, hirudin and argatroban, including pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and European Patent Application Publication Number 293 881 A2, the disclosures of which are hereby incorporated herein by reference. Other suitable boroarginine derivatives and boropeptide thrombin inhibitors include those disclosed in PCT Application Publication Number 92/07869 and European Patent Application Publication Number 471 651 A2, the disclosures of which are hereby incorporated herein by reference, in their entirety.

The phrase "thrombolytic" or "fibrinolytic agents" or "thrombolytics" or "fibrinolytics", as used herein, denotes agents that lyse blood clots (thrombi). Such agents include tissue plasminogen activator, anistreplase, urokinase or streptokinase, including pharmaceutically acceptable salts or prodrugs thereof. Tissue plasminogen activator (tPA) is commercially available from Genentech Inc., South San Francisco, Calif. The term anistreplase, as used herein, refers to anisoylated plasminogen streptokinase activator complex, as described, for example, in European Patent Application No. 028,489, the disclosures of which are hereby incorporated herein by reference herein, in their entirety. Anistreplase is commercially available as Eminase™. The term urokinase, as used herein, is intended to denote both dual and single chain urokinase, the latter also being referred to herein as prourokinase.

Administration of the compounds of Formula I of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

GPIIb/IIIa is known to be overexpressed in metastatic tumor cells. The compounds or combination products of the present invention may also be useful for the treatment, including prevention, of metastatic cancer.

The compounds of the present invention are also useful as standard or reference compounds, for example as a quality standard or control, in tests or assays involving the binding of fibrinogen to platelet GPIIb/IIIa. Such compounds may be provided in a commercial kit, for example, for use in pharmaceutical research involving GPIIb/IIIa. The compounds of the present invention may also be used in diagnostic assays involving platelet GPIIb/IIIa.

The compounds herein described may have asymmetric centers. Unless otherwise indicated, all chiral, diastereomeric and racemic forms are included in the present invention. Geometric isomers of C=N double bonds can also be present in the compounds described herein, and all such stable isomers are contemplated in the present invention. It will be appreciated that compounds of the present invention that contain asymmetrically substituted carbon atoms may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

As used herein, "pharmaceutically acceptable salts" refer to derivatives of the disclosed compounds wherein the parent compound of Formula I is modified by making acid or base salts of the compound of Formula I. Examples of pharmaceutically acceptable salts include, but are not limited to, mineral or organic acid salts of basic residues such as amines; alkali or organic salts of acidic residues such as carboxylic acids; and the like.

"Prodrugs" are considered to be any covalently bonded carriers which release the active parent drug according to Formula I in vivo when such prodrug is administered to a mammalian subject. Prodrugs of the compounds of Formula I are prepared by modifying functional groups present in the compounds in such a way that the modifications are cleaved, either in routine manipulation or in vivo, to the parent compounds. Prodrugs include compounds of Formula I wherein the amino or carboxyl groups are bonded to any group that, when administered to a mammalian subject, cleaves to form a free amino or carboxyl group, respectively. Examples of representative carboxyl prodrugs are included under the definition of Y. Examples of representative amino prodrugs are included under the definition of $R^1$.

The pharmaceutically acceptable salts of the compounds of Formula I include the conventional non-toxic salts or the quaternary ammonium salts of the compounds of Formula I formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammoinum hydroxide and the like.

As discussed above, pharmaceutically acceptable salts of the compounds of the invention can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

SYNTHESIS

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The following abbreviations are used herein:

| | |
|---|---|
| α-Ala | 3-aminopropionic acid |
| Boc | tert-butyloxycarbonyl |
| Boc$_2$O | di-tert-butyl dicarbonate |
| BOP | benzotriazolyl-N-oxy-tris(dimethylamino)-phosphonium hexafluorophosphate |
| pyBOP | benzotriazolyl-N-oxy-tris(pyrrolidino) -phosphonium hexafluorophosphate |
| BSTFA | N,O-bis (trimethylsilyl)trifluoromethyl-acetamide |
| Cbz | benzyloxycarbonyl |
| DCC | 1,3-dicyclohexylcarbodiimide |
| DEAD | diethyl azodicarboxylate |
| DEC | 1-(3-dimethylminopropyl)-3-ethylcarbodiimide hydrochloride |
| DIEA | diisopropylethylamine |
| DCHA | dicyclohexylamine |
| DCM | dichloromethane |
| DMAP | 4-dimethylaminopyridine |
| DMF | N, N-dimethylformamide |
| EtOAc | ethyl acetate |
| EtOH | ethyl alcohol |
| HOBt | 1-hydroxybenzotriazole |
| IBCF | iso-butyl chloroformate |
| LAH | lithium aluminum hydride |
| NCS | N-chlorosuccinimide |
| NMM | N- methylmorpholine |
| PPh3 | triphenylphosphine |
| pyr | pyridine |
| TBTU | 2-(1H-benzotriazol-1-yl)-1,1,3,3-tetramethyluronium tetrafluoroborate |
| TEA | triethylamine |
| TFA | trifluoroacetic acid |
| THF | tetrahydrofuran |
| Z | benzyloxycarbonyl |

A convenient method for the synthesis of the compounds of this invention utilizes a dipolar cycloaddition of nitrile oxides with appropriate dipolarophiles to prepare the isoxazoline rings present in compounds of Formula I (for reviews of 1,3-dipolar cycloaddition chemistry, see 1,3-Dipolar Cycloaddition Chemistry (Padwa, ed.), Wiley, N.Y., 1984; Kanemasa and Tsuge, *Heterocycles* 1990, 30, 719).

Scheme I describes one synthetic sequence to the compounds of the second embodiment of this invention. An appropriately substituted hydroxylamine is treated with NCS in DMF according to the method of Liu, et al. (*J. Org. Chem.* 1980, 45, 3916). The resulting hydroximinoyl chloride is then dehydrohalogenated in situ using TEA to give a nitrile oxide, which undergoes a 1,3-dipolar cycloaddition to a suitably substituted alkene such as vinylacetic acid or esters thereof, to afford the isoxazoline. Alternatively, the oxime may be oxidatively chlorinated, dehydrochlorinated and the resulting nitrile oxide trapped by a suitable alkene under phase transfer conditions according to the method of Lee (*Synthesis* 1982, 508). Hydrolysis of the ester, when present, using conventional methods known to one skilled in the art of organic synthesis gives the desired acids. Intermediates containing alkali-sensitive functionality, such as nitrile, may be deesterified with excellent chemoselectivity using sodium trimethylsilanolate according to the procedure of Laganis and Ehenard (*Tetrahedron Lett.* 1984, 25, 5831) or with aqueous hydrochloric acid. Coupling of the resulting acids to an appropriately substituted α, β-diamino ester using standard coupling reagents, such as TBTU, BOP, pyBOP or DCC/HOBt, affords a nitrile-amide. The nitrile is then converted to the amidine via the imidate or thioimidate under standard conditions. Hydrolysis of the ester, if desired, may be carried out using basic (LiOH, THF/H$_2$O) or acidic (aqueous hydrochloric acid) conditions or with esterases.

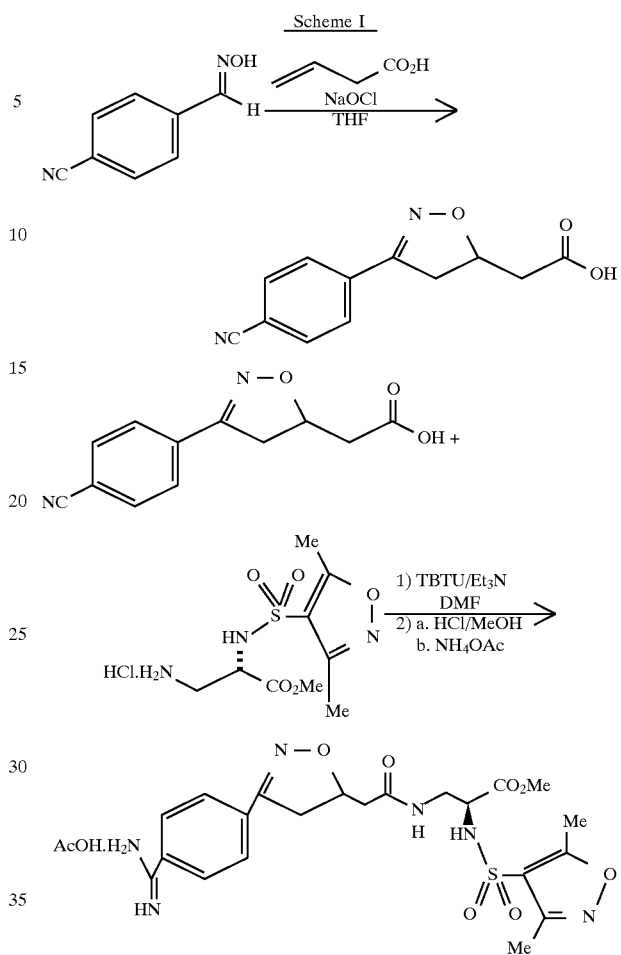

Scheme I

An example of a related method of preparation for compounds within the scope of the present invention is illustrated in Scheme II. Conversion of 3-(4-cyanophenyl)-isoxazolin-5-ylacetic acid to the corresponding amidine, followed by protection as the Boc-derivative and saponification provides 3-(4-Boc-amidinophenyl)isoxazolin-5-ylacetic acid which is coupled with α, β-diamino acid esters as shown. Saponification and acidic deprotection yields the free acids.

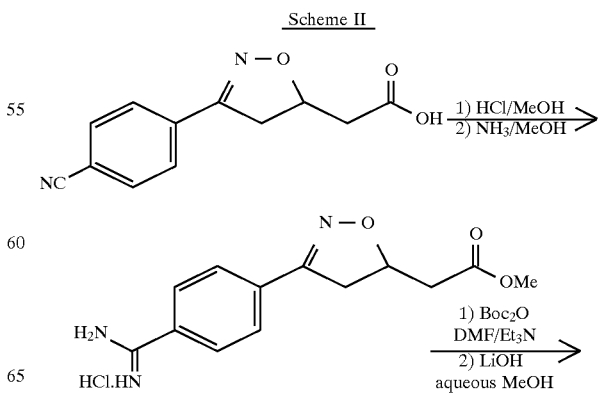

Scheme II

-continued
Scheme II

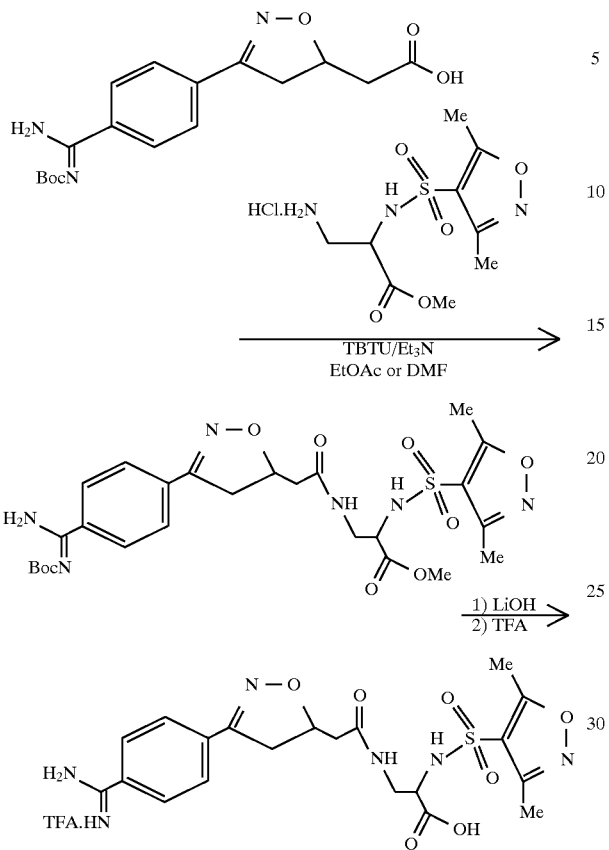

Methyl N²-(3,5-Dimethylisoxazole-4-sulfonyl)-2,3-diaminopropionates are available from N²-Cbz-2,3-diaminopropionic acids as shown in Scheme III for the L-isomer.

Scheme III

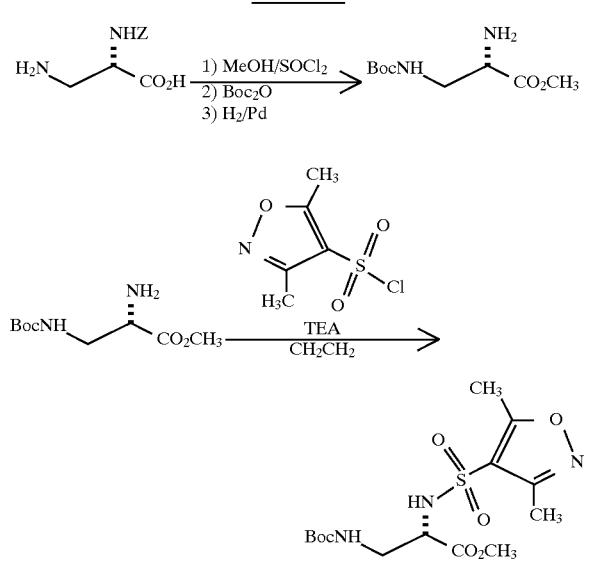

-continued
Scheme III

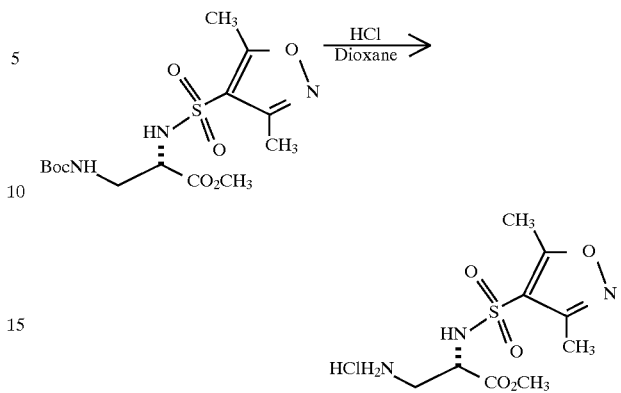

The compounds of the present invention where $R^1$ is an amidine prodrug, e.g. alkoxycarbonyl or other, may be prepared by reacting the free amidines with an activated carbonyl derivative, such as an alkyl chloroformate. In compounds of the present invention, the conversion of the free amidines to such acyl-nitrogen groups may optionally be performed prior to coupling an isoxazoline acetic acid with α, β-diamino acids as illustrated with t-butyloxycarbonyl in Scheme II.

The compounds of the present invention wherein Y is an oxyalkoxy group, e.g. alkoxycarbonyloxyalkoxy, may be prepared by reacting a suitably protected carboxylic acid of Formula I with an e.g. an alkoxycarbonyloxyalkyl chloride in the presence of an iodide source, such as tetrabutylammonium iodide or potassium iodide, and an acid scavenger, such as triethylamine or potassium carbonate, using procedures known to those skilled in the art.

The compounds of this invention and their preparation can be further understood by the following procedures and examples, which exemplify but do not constitute a limit of their invention.

EXAMPLE 1

Methyl N²-(3,5-Dimethylisoxazole-4-sulfonyl)(S)-2,3-diaminopropionate Hydrochloride Salt Part A: Methyl N²-Cbz-L-2,3-diaminopropionate HCl Salt To a solution of N²-Cbz-L-2,3-diaminopropionic acid (Bachem, 220 g, 0.923 mol) in MeOH (2 L) at 0° C. was added thionyl chloride (76 mL, 1.04 mol) over 20 min. The solution was warmed to room temperature overnight (18 h) and then concentrated to give a solid. The solid was crystallized from CHCl₃-MeOH to give 172 g (64%) of the desired ester; ¹H NMR (DMSO-d₆) δ 8.38 (b, 3H), 7.96 (d, 1H), 7.38 (m, 5H), 5.05 (s, 2H), 4.44 (m, 1H), 3.66 (s, 3H), 3.14 (m, 2H).

Part B: Methyl N²-Cbz-N³-Boc-L-2,3-diaminopropionate

To a solution of methyl N²-Cbz-(S)-2,3-diaminopropionate HCl salt (172 g, 0.596 mol) and di-tert-butyl dicarbonate (129.05 g, 0.591 mol) in CH₂Cl₂ (2 L) cooled in an ice bath was added a saturated solution of NaHCO₃ (1200 mL, 0.96 mol) and the solution was warmed to room temperature overnight (18 h). The layers were separated and the aqueous washed with CH₂Cl₂ (2×500 mL). The combined organic was washed with brine, dried (MgSO₄), and concentrated. The resulting white solid was triturated with hexanes (3×500 mL) and dried under vacuum, giving 195.99 g (93%) of the desired material; ¹H NMR (DMSO-d₆): δ 7.60 (d, 1H), 7.35 (m, 5H), 6.88 (t, 1H), 5.02 (s, 2H), 4.14 (m, 1H), 3.60 (s, 3H), 3.28 (m, 2H), 1.37 (s, 9H).

Part C: Methyl N³-Boc-(S)-2,3-diaminopropionate

To a solution of methyl N²-Cbz-N³-Boc-(S)-2,3-diaminopropionate. (54.7 g, 0.155 mol) in EtOH (300 mL) was added 10% Pd/C (4.0 g). The mixture was placed on a Parr apparatus and hydrogenated at 50 p.s.i. overnight (18 h). The catalyst was filtered through diatomaceous earth, the filter cake washed with EtOH (3×50 mL) and the filtrate was concentrated in vacuo and placed under vacuum to give 32.63 g (96%) of the free base amine as a golden, viscous liquid; $^1$H NMR (DMSO-$d_6$): δ 8.20(s, 1H), 6.90 (t, 1H), 5.36 (b, 3H), 3.61 9s, 3H), 3.51 (t, 1H), 3.18 (t, 2H), 1.38 (s, 9H).

Part D: Methyl N²-(3,5-dimethylisoxazole-4-sulfonyl)-N³-Boc-(S)-2,3-diaminopropionate To a solution of methyl N³-Boc-(S)-2,3-diaminopropionate (22.05 g, 101 mmol) in $CH_2Cl_2$ (300 mL) at 0° C. was added 3,5-dimethylisoxazole-4-sulfonyl chloride (20.0 g, 102 mmol). To this mixture was added over 30 min a solution of $Et_3N$ (16.2 mL, 116 mmol) in $CH_2Cl_2$ (50 mL) and the resulting mixture allowed to warm to room temperature overnight (18 h). The mixture was washed with 0.1M HCl, sat. $NaHCO_3$ and brine, dried ($MgSO_4$), and concentrated in vacuo. Purification using flash chromatography (0–8% MeOH—$CHCl_3$) followed by concentration of the appropriate fractions in vacuo and placing the residue under vacuum until constant weight was achieved then gave 31.56 g (83%) of the desired sulfonamide as a viscous oil; $^1$H NMR (300 MHz, $CDCl_3$) δ 6.14 (bs, 1H), 5.04 (bt, 1H), 3.97 (bs, 1H), 3.66 (s, 3H), 3.50 (m, 2H), 3.15 (bq, J=7.3 Hz, 1H), 2.62 (s, 3H), 2.42 (s, 3H), 1.43 (s, 9H).

Part E: Methyl N²-(3,5-Dimethylisoxazole-4-sulfonyl)(S)-2,3-diaminopropionate Hydrochloride Salt To neat methyl N²-(3,5-dimethylisoxazole-4-sulfonyl)-N³-Boc-(S)-2,3-diaminopropionate (31.56 g, 83.62 mmol) was added 4M HCl/dioxane (100 mL, 400 mmol). The resulting solution was stirred at room temperature for 4 h, then it was concentrated in vacuo, giving an oil. Trituration with ether (3×10 mL) followed by drying under vacuum afforded 28.24 g of the desired amine, still containing 30 mol % residual dioxane (75% yield); $^1$H NMR (300 MHz, $CDCl_3$, poorly resolved) δ 8.23 (bs, 3H), 8.05 (bs, 1H), 4.47 (bs, 1H), 3.64 (m, 2H), 3.50 (m, 2H), 3.58 (s, 3H), 3.13 (m, 1H), 2.61 (s, 3H), 2.43 (s, 3H).

EXAMPLE 2

4-Cyanobenzaldoxime

This material was prepared from 4-cyanobenzaldehyde according to Kawase and Kikugawa (*J. Chem. Soc., Perkin Trans I* 1979, 643). To a solution of 4-cyanobenzaldehyde (1.31 g, 10 mmol) in 1:1EtOH:pyridine (10 mL) was added hydroxylamine hydrochloride (0.70 g, 10 mmol). The resulting solution was stirred at room temperature for 18 h and was concentrated in vacuo to one-half volume. To this solution was added ice water, causing the product to crystallize from solution. Recrystallization from EtOH—water followed by drying over $P_2O_5$ afforded 1.46 g (100%) of the desired oxime; mp: 167.8–169.4° C.

EXAMPLE 3

3-(4-Cyanophenyl)isoxazolin-5(R,S)-ylacetic Acid

To a solution of 4-cyanobenzaldoxime (see Ex 2) (312 g, 2.13 mol) in tetrahydrofuran (3 L) at room temperature was added vinylacetic acid (552 g, 6.41 mol). The yellow solution was cooled in an ice bath and sodium hypochlorite solution (5200 mL)was added in a dropwise fashion over 2 h. After stirring overnight at room temperature the reaction was quenched with a 5% citric acid solution and diluted with 200 mL ether. The layers were separated and the aqueous acidified to pH 4 using citric acid. The acid layer was washed twice with 200 mL ether, the ether layers combined and extracted with saturated sodium bicarbonate solution. After acidifying the basic layer with citric acid, the product was extracted into 400 mL ether. The organic phase was washed three times with 150 mL water, once with brine, dried ($MgSO_4$) and concentrated to give 220 g of 3-(4-cyanophenyl)isoxazolin-5-ylacetic acid as a white solid. Recrystallization from 25% water/ethanol yielded 165 g of analytically pure material; $^1$H NMR (300 MHz, $CDCl_3$) δ 7.77–7.76 (d, J=1.8 Hz, 2H), 7.72–7.71 (d, J=1.8 Hz, 2H), 5.22–5.14 (m, 1H), 3.63–3.54 (dd, J=10.6 Hz, 16.8 Hz, 1H), 3.19–3.11 (dd, J=7.3 Hz, 16.8 Hz, 1H), 3.00–2.93 (dd, J=6.2 Hz, 16.5 Hz, 1H), 2.79–2.72 (dd, J=7.3 Hz, 16.5 Hz, 1H); IR (KBr): 3202, 2244, 1736, 1610, 1432, 1416, 1194, 1152, 928, 840, 562 $cm^{-1}$. Anal. Calcd for $C_{12}H_{10}N_2O_3$: C, 62.61; H, 4.38; N, 12.17. Found: C, 62.37; H, 4.47; N, 11.71.

EXAMPLE 4

3-(4-cyanophenyl)isoxazolin-5(R)-ylacetic acid and 3-(4-cyanophenyl)isoxazolin-5(S)-ylacetic acid These materials were obtained by resolution of 3-(4-cyanophenyl)isoxazolin-5(R,S)-ylacetic acid (Example 3). The racemic compound was resolved on a 2×50 cm Chiralpak AD column using 0.1% TFA/EtOH at 10° C. to give the 5(S) isomer (faster eluting) and 5(R) isomer (slower eluting). Alternatively, the isomers were resolved by crystallization of the cinchonidine salt of the 5(S) isomer of the isoxazolines from acetone, leaving the 5(R) isomer in the mother liquor. The absolute stereochemistry of the crystalline cinchonidine salt was determined by X-ray crystallography to be 5(S).

EXAMPLE 5

3-(4-N-t-Butoxycarbonylamidinophen-yl)isoxazolin-5(R,S)-ylacetic Acid

Part A: Methyl 3-(4-Methoxyiminophenyl)isoxazolin-5(R,S)-ylacetate. Hydrochloride Salt A suspension of 3-(4-cyanophenyl)-(5R,S)-isoxazolin-5-ylacetic acid (prepared in Example 3, 23.1 g, 100 mmol) in 200 mL of anhydrous methanol was chilled in an ice bath and dry HCl gas was bubbled through the reaction mixture until a clear solution was obtained. The total addition time was about three hours. The reaction flask was sealed, and the reaction mixture was allowed to warm to room temperature, with stirring, over a period of about 24 h. At this point, the methanolic solution was poured into 600 mL of anhydrous ether, precipitating the product, and the resulting slurry was chilled to −25° C. for 2 ½ h. The slurry was then diluted with an additional 100 mL of chilled anhydrous ether. The precipitate was filtered, washed with two 100 mL portions of chilled anhydrous ether, and suction dried under nitrogen to afford 23.3 g (73%) of the hydrochloride salt; $^1$H NMR (300 MHz, $CDCl_3$) δ 12.9 (bs, 1H) 12.2 (bs, 1H), 8.46 (d, J=8.8 Hz, 2H), 7.86 (d, J=8.8 Hz, 2H), 5.20 (bm, 1H), 4.59 (s, 3H), 3.74 (s, 3H), 3.53 (dd, J=16.8, 10.6 Hz, 1H), 3.15 (dd, J=16.8, 7.7 Hz, 1H), 2.90 (dd, J=16.1, 6.2 Hz, 1H), 2.70 (dd, J=16.1, 7.3 Hz, 1H), 1.77 (bs, 1H); CIMS ($NH_3$, e/z, relative abundance): 277 $(M+H)^+$, 100%.

Part B: Preparation of Methyl 3-(4-Amidinophenyl)-isoxazolin-5(R,S)-ylacetate. Hydrochloride Salt A suspension of methyl 3-(4-methoxyiminophenyl)-(5R,S)-isoxazolin-5-ylacetate hydrochloride (22.9 g, 73.0 mmol)

in 500 mL of 1M ammonia in anhydrous methanol was stirred at room temperature for 14 h during which time all solids dissolved. The solution was concentrated in vacuo to give 22.1 g (100%) of crude hydrochloride salt as a tan solid; $^1$H NMR (300 MHz, CDCl$_3$) δ 9.6–9.2 (b), 7.91 (d, J=8.8, 2H), 7.87 (d, J=8.8, 2H), 5.08 (bm, 1H), 3.64 (s, 3H), 3.3–3.1 (m, 2H), 2.8 (m, 2H); MS (ESI, e/z, relative abundance): 264, (M+H)$^+$, 100%.

Part C: Preparation of Methyl 3-(4-N-Butoxycarbonyl-amidinophenyl)isoxazolin-5(R,S)-ylacetate To a solution of 21.6 g (72.5 mmol) of methyl 3-(4-amidinophenyl)isoxazolin-5-ylacetate in DMF (350 mL) cooled with an ice bath was added triethylamine (20.2 mL, 145 mmol) and di-tert-butyl dicarbonate (17.4 g, 79.8 mmol). The mixture was warmed to room temperature and stirred for 16 hours. The reaction mixture was poured into water (1500 mL) while stirring. A white precipitate formed and was then filtered and dried on the filter under nitrogen to give 19.6 g (74.8%) of the title compound as a white solid; MS (ESI, e/z, relative abundance): 362 (M+H)$^+$; 306 (M+H–tBu)$^+$; $^1$H NMR (300 MHz, d$_6$-DMSO) δ 7.90 (d, J=8.4 Hz, 2H), 7.70 (d, J=8.4 Hz, 2H), 5.14 (m, 1H), 3.74 (s, 3H), 3.56 (dd, J=6.8, 6.8 Hz, 1H), 3.14 (dd, J=6.8, 6.8 Hz, 1H), 2.90 (dd, J=6.1, 6.1 Hz, 1H), 2.68 (dd, J=6.1, 6.1 Hz, 1H), 1.56 (s, 9H); $^{13}$C NMR (60 MHz, d$_6$-DMSO): δ 170.93, 165.76, 164.04, 156.86, 136.24, 132.79, 128.51, 126.91, 78.35, 77.89, 51.98, 39.58, 39.31, 28.46.

Part D: 3-(4-N-t-Butoxycarbonylamidinophenyl)isoxazolin-5(R,S)-ylacetic Acid

To a solution of 18.95 g (52.4 mmol) of methyl 3-(4-N-butoxycarbonylamidinophenyl)isoxazolin-5-ylacetate in methanol (500 mL) was added a solution of lithium hydroxide monohydrate (2.42 g, 57.7 mmol) in water (75 mL) at 22° C. The mixture was stirred at 22° C. for 16 h and then filtered; the filtrate was evaporated under reduced pressure to remove methanol. The residual aqueous phase was cooled with an ice bath and acidified with 6N and 1N HCl to pH 4. A white solid precipitated and it was left at –4° C. overnight. The solid was filtered and dried on the filter under nitrogen to give 17.74 g (97.4%) of the title compound as an off-white powder; $^1$H NMR (300 MHz, d$_6$-DMSO) δ 7.94 (d, J=8.4 Hz, 2H), 7.78 (d, J=8.4 Hz, 2H), 5.04 (m, 1H), 3.62 (dd, J=6.8, 7.2 Hz, 1H), 3.22 (dd, J=7.2, 7.2 Hz, 1H), 2.68 (d, J=7.0 Hz, 2H), 1.50 (s, 9H); $^{13}$C NMR (60 MHz, d$_6$-DMSO): δ 171.91, 165.58, 158.61, 156.76, 133.87, 132.78, 129.43, 126.87, 81.55, 78.39, 40.44, 39.30, 28.27; MS (ESI, m/e, relative intensity): 348 (M+H)$^+$; 292 (M+H–tBu)$^+$.

EXAMPLE 6

N$^2$-(3,5-dimethylisoxazole-4-sulfonyl)-N$^3$-[3-(4-amidinophenyl)isoxazolin-5(R,S)-ylacetyl]-(S)-2,3-diaminopropionate Trifluoroacetate Salt Part A: Methyl N$^2$-(3,5-Dimethylisoxazole-4-sulfonyl)-N$^3$ [3-(4-N-t-butoxycarbonylamidinophenyl)isoxazolin-5(R,S)-ylacetyl]-(S)-2,3-diaminopropionate Methyl N$^2$-(3,5-dimethylisoxazole-4-sulfonyl)-N$^3$-Boc-(S)-2,3-diaminopropionate (prepared in Example 1, 526 mg, 1.40 mmole) was stirred with 4M HCl/dioxane (10 mL, 40 mmol) at 25° C. After 2.5 h, the volatiles were removed in vacuo, and residual HCl/dioxane was removed by repeated addition of toluene and evaporation. To the residue was added 3-(4-N-t-butoxycarbonylamidinophenyl)isoxazolin-5(R,S)-ylacetic acid (prepared in Example 5, 510 mg, 1.47 mmol), TBTU (480 mg, 1.50 mmole) and DMF (15 mL). Triethylamine (0.830 mL, 603 mg, 5.97 mmole) was added and the reaction mixture was stirred at 25° C. overnight. The mixture was diluted with water (70 mL) extracted with 3× ethyl acetate. The combined organic extracts were washed with 2× water, 5% pH 4 potassium hydrogen phthalate buffer (25 mL), 5% aqueous sodium bicarbonate (25 mL) and brine. After drying over MgSO$_4$, removal of volatiles and purification by flash chromatography (ethyl acetate) provided 0.598 g of the desired product in 96% purity, as assessed by analytical HPLC (4.6 mm×25 cm C18 reverse phase, 1 mL/min, 0.05% TFA/10–90% AcCN/water gradient over 20 min, product at 12.9 min); $^1$H NMR (300 MHz, CDCl$_3$) δ 7.84 (m, 2H), 7.63 (m, 2H), 6.52 (bm, 1H), 6.07 (bd, 1H), 5.11 (bm, 1H), 4.02 (bm, 1H), 3.66/3.67 (2s, 3H, diastereomers, methyl ester), 3.67–3.45 (m, 3H), 3.15 (m, 1H), 2.60/2.61 (2s, 3H, diastereomers, isoxazole methyl), 2.76–2.55 (m, 2H), 2.38/2.41 (2s, 3H, diastereomers, isoxazole methyl), 1.56 (s, 9H, t-Bu); MS (ESI): m/e 607.2 (M+H)$^+$.

Part B: N$^2$-(3,5-Dimethylisoxazole-4-sulfonyl)-N$^3$[3-(4-N-t-butoxycarbonylamidinophenyl)isoxazolin-5(R,S)-ylacetyl]-(S)-2,3-diaminopropionate To a solution of 200 mg (0.329 mmole) of methyl N$^2$-(3,5-dimethylisoxazole-4-sulfonyl)-N$^3$[3-(4-N-t-butoxycarbonyl-amidinophenyl)isoxazolin-5(R,S)-ylacetyl]-(S)-2,3-diamino-propionate in 15 mL of THF/MeOH/water 1:1:1 was added 138 mg (3.29 mmole) of LiOH. After 2 h, analytical HPLC (see conditions in Part A, product at 11.7 min) indicated the reaction was 97% complete. Removal of volatiles and purification by flash chromatography provided 0.164 g 91% pure (see HPLC conditions in Part A) of the desired product as a mixture of free acid and lithium salt (as indicated by 0.55% Li by elemental analysis); $^1$H NMR (300 MHz, DMSO-d$_6$) δ 8.02 (d, J=8.0 Hz, 2H), 7.96 (m, 1H), 7.75 (dd, J=1.5, 8.4 Hz, 2H), 5.02 (m, 1H), 3.58–3.08 (m, 5H), 2.55 (s, 3H, isoxazole methyl), 2.60–2.37 (m, 2H), 2.34 (s, 3H, isoxazole methyl), 1.45 (s, 9H, t-Bu); MS (ESI): m/e 593.3 (M+H)$^+$, m/e 493.2 (M-Boc)$^+$.

Part C: N$^2$-(3,5-dimethylisoxazole-4-sulfonyl)-N$^3$-[3-(4-amidinophenyl)isoxazolin-5(R,S)-ylacetyl]-(S)-2,3-diaminopropionate Trifluoroacetate Salt A solution of 137 mg (0.231 mmole) of N$^2$-(3,5-dimethylisoxazole-4-sulfonyl)-N$^3$ [3-(4-N-t-butoxycarbonyl-amidinophenyl)isoxazolin-5(R,S)-ylacetyl]-(S)-2,3-diamino-propionate in 4 mL of CH$_2$Cl$_2$ and 2 mL of TFA was stirred for 4 h, then diluted with 60 mL of ether. The precipitate was dried to give 0.103 g of the desired product as a white solid, which was determined to be 96% pure by analytical HPLC (see HPLC conditions in Part A); $^1$H NMR (300 MHz, DMSO-d$_6$) δ 9.79 (bs, 1H), 9.72 (bs, 1H), 9.29 (bs, 2H), 8.25 (bs, 1H), 8.16 (m, 1H), 7.87 (s, 4H), 5.02 (bm, 1H), 3.78 (bs, 1H), 3.60–3.08 (m, 4H), 2.54 (s, 3H, isoxazole methyl), 2.34 (s, 3H, isoxazole methyl), 2.62–2.34 (m, 2H); MS (ESI): m/e 493.3 (M+H)$^+$; HRMS (FAB): m/e calculated for C$_{20}$H$_{25}$N$_6$O$_7$S (M+H)$^+$493.150544; found 493.148681.

EXAMPLE 7

Separation of N$^2$-(3,5-Dimethylisoxazole-4-sulfonyl)-N$^3$-[3-(4-amidinophenyl)isoxazolin-5(S)-ylacetyl]-(S)-2,3-diamino-propionate Trifluoroacetate Salt and N$^2$-(3,5-Dimethyl-isoxazole-4-sulfonyl)-N$^3$-[3-(4-amidinophenyl) isoxazolin-5(R)-ylacetyl]-(S)-2,3-diaminopropionate Trifluoroacetate Salt by Chiral HPLC The mixture of the title compounds prepared in Example 6 was separated by preparative chiral supercritical fluid chromatography (SFC) on a Chiracel OD 2×25 cm column, eluting with 0.1% TFA/27% MeOH/73% $CO_2$ at 190 atm, using a flow rate of 18 mL/min and injections of approximately 13 mg. The column temperature is maintained at 25° C. and the detector is set at 280 nm. The fractions containing the first eluting isomer are combined and concentrated to yield the TFA salt of the isoxazoline-5(S) isomer, while the fractions containing the second eluting isomer are combined to yield the isoxazoline-5(R) isomer. Diastereomeric purity was determined to be >99% (S,S vs. R,S diastereomers) using SFC employing a Chiracel OD 0.46×25 cm column eluting with 0.1% TFA/22% MeOH/78% $CO_2$ at 150 atm, using a flow rate of 2.0 mL/min. The column temperature is maintained at 30° C. and the detector is set at 280 nm. The absolute stereochemistry of the two diastereomers was determined by comparison with material prepared independently from 3-(4-cyanophenyl)isox-azolin-5(R)-ylacetic acid (Example 8).

EXAMPLE 8

$N^2$-(3,5-Dimethylisoxazole-4-sulfonyl)-$N^3$-[3-(4-amidinophenyl)isoxazolin-5(R)-ylacetyl]-(S)-2,3-diaminopropionic Acid Methanesulfonate Salt Part A: Methyl $N^2$-(3,5-Dimethylisoxazole-4-sulfonyl)-$N^3$[3-(4-(cyanophenyl)isoxazolin-5(R)-ylacetyl]-(S)-2,3-diaminopropionate To a suspension of 3-(4-cyanophenyl)isoxazolin-5(R)-ylacetic acid (prepared in Example 4, 252 mg, 0.725 mmol), methyl $N^2$-(3,5-dimethylisoxazole-4-sulfonyl-(S)-2,3-diaminopropionate hydrochloride (prepared in Example 1, 28.24 g, 70% purity, 63.0 mmol) in DMF (200 mL) was added TBTU (28.90 g, 90 mmol). The mixture was cooled to 0° C. and $Et_3N$ (31.4 mL, 225 mmol) was added dropwise. The resulting mixture was allowed to warm to room temperature overnight (18 h), then was diluted with EtOAc (500 mL). It was washed with water (4×200 mL), sat. $NaHCO_3$ (100 mL), sat. NaCl (100 mL) and dried ($MgSO_4$). Concentration in vacuo followed by placing the material under vacuum until constant weight was achieved afforded 25.06 g (81%) of the desired amide; $^1H$ NMR (300 MHz, $CDCl_3$) δ 8.77 (bs, 1H), 8.22 (t, J=5.9 Hz, 1H), 5.02 (m, 1H), 3.98 (t, J=7.0 Hz, 1H), 3.55 (dd, J=17.2, 10.6 Hz, 1H), 3.48 (s, 3H), 3.42 (m, 1H), 3.16 (m, 2H), 2.54 (s, 3H, coincident with m, 1H, DMSO-$d_5$), 2.37 (dd, J=14.6, 7.0 Hz, 1H), 2.33 (s, 3H).

Part B: Methyl $N^2$-(3,5-Dimethylisoxazole-4-sulfonyl)-$N^3$[3-(4-amidinophenyl)isoxazolin-5(R)-ylacetyl]-(S)-2,3-diaminopropionate Acetate Salt Into a solution of methyl $N^2$-(3,5-dimethyl-isoxazole-4-sulfonyl)-$N^3$[3-(4-(cyanophenyl)isoxazolin-5(R)-ylacetyl]-(S)-2,3-diaminopropionate (25.06 g, 51.17 mmol) in anhydrous MeOH (750 mL) at 0° C. was bubbled HCl gas for 3 hours. The resulting solution was then allowed to warm to room temperature overnight (18 h), after which the solvent was evaporated in vacuo, to give an oil. The oily residue was triturated with ether (3×100 mL) and the resulting solid placed under vacuum until constant weight was achieved. The crude imidate was then dissolved in MeOH (1 L) and ammonium acetate (20.0 g, 259 mmol) added. The resulting mixture was stirred at room temperature for 18 h, then concentrated in vacuo. The residue was then crystallized from EtOH, giving 21.75 g of crude amidine. A portion of this material (8.5 g) was purified using flash chromatography (20% MeOH-EtOAc) to give 3.77 g (33%) of 97.6% pure amidine (analytical HPLC: 4.6 mm×25 cm C18 reverse phase, 1 mL/min, 0.05% TFA/10–90% AcCN/water gradient over 20 min.); $^1H$ NMR (300 MHz, DMSO-$d_6$) δ 8.26 (bt, 1H), 7.86 (m, 4H), 5.01 (m, 1H), 3.96 (t, J=6.6 Hz, 1H), 3.56 (dd, J=17.2, 10.6 Hz, 1H), 3.48 (s, 3H, coincident with m, 1H), 3.18 (m, 2H), 2.53 (s, 3H, coincident with m, 1H, DMSO-$d_5$), 2.54 (s, 3H), 2.36 (dd, J=14.6, 7.0 Hz, 1H), 2.32 (s, 3H), 1.74 (s, 3H); MS (ESI): m/e 507.3 (M+H)$^+$.

Part C: $N^2$-(3,5-Dimethylisoxazole-4-sulfonyl)-$N^3$[3-(4-amidinophenyl)isoxazolin-5(R)-ylacetyl]-(S)-2,3-diaminopropionic Acid (Enzymatic Hydrolysis)

To a solution of methyl $N^2$-(3,5-dimethylisoxazole-4-sulfonyl-$N^3$[3-(4-amidinophenyl)isoxazolin-5(R)-ylacetyl]-(S)-2,3-diaminopropionate HOAc salt (1.866 g, 3.29 mmol) in 0.4N Hepes buffer (pH 7.1, 220 mL, 15 mmol) was added rabbit liver esterase (3.6M crystalline suspension in ammonium sulfate, 2000 units, Sigma). The resulting solution was incubated at 37° C. for 60 hours. Protein was removed from the reaction mixture by ultra filtration (Amicon YM-10 membrane), and the filtrate was then concentrated in vacuo and lyophilized. Purification using a reverse phase silica column (5×9.5 cm in water; crude product loaded as an aqueous solution followed by elution with water (1200 mL) and by 500 mL each of 5, 10, 20 and 30% $CH_3CN$—$H_2O$. Fractions containing the desired product were pooled, acetonitrile was removed and the aqueous solution lyophilized to yield 1.5 g (93%) of pure zwitterion; $^1H$ NMR (300 MHz, DMSO-$d_6$) δ 7.93 (t, 1H), 7.76 (s, 4H), 4.98 (m, 1H), 3.17–3.50 (m, 5H, coincident with water), 2.66 (dd, 1H), 2.56 (s, 3H), 2.35 (s, 3H), 2.36 (dd, 1H); MS (ESI): m/e 493.3 (M+H)$^+$.

Part D: $N^2$-(3,5-Dimethylisoxazole-4-sulfonyl)-$N^3$[3-(4-amidinophenyl)isoxazolin-5(R)-ylacetyl]-(S)-2,3-diaminopropionic Acid Methanesulfonic Acid Salt To a solution of the zwitterion (2.75 g, 5.43 mmol) in 50% $CH_3CN$—$H_2O$ (135 mL) was added methanesulfonic acid (0.57 g, 5.97 mmol). The reaction mixture was stirred at room temperature for 1 h, resulting in a clear solution. Solvents were removed in vacuo and the residue placed under vacuum for several hours. The crude mesylate was dissolved in hot acetone and water until the solution was clear (120 mL total volume). After hot filtration the solution was allowed to cool slowly and was then refrigerated for 24 h. The resulting white precipitate was filtered and dried under vacuum, affording 1.72 g (52%) of the title compound; $^1H$ NMR (300 MHz, DMSO-$d_6$) δ 9.37 (bs, 2H), 9.03 (bs, 2H), 8.57 (d, J=9.5 Hz, 1H), 8.23 (t, J=5.9 Hz, 1H), 7.88 (s, 4H), 5.03 (m, 1H), 3.91 (m, 2H), 3.57 (dd, J=17.2, 10.6 Hz, 1H), 3.44 (m, 1H), 3.21 (dd, J=17.6, 7.7 Hz, 1H), 3.09 (m, 1H), 2.58 (dd, J=14.6, 6.6 Hz, 1H), 2.54 (s, 3H), 2.38 (dd, J=14.6, 7.3 Hz, 1H), 2.33 (s, 3H, MsOH); MS (ESI): m/e 493.2 (M+H)$^+$; Anal. Calcd. for $C_{21}H_{28}N_6O_{10}S_2$: C, 42.85; H, 4.79; N, 14.05; S, 10.89. Found: C, 42.45; H, 4.74; N, 14.05; S, 11.19.

EXAMPLE 9

$N^2$-(3,5-dimethylisoxazole-4-sulfonyl)-$N^3$-[3-(4-amidinophenyl)isoxazolin-5(R)-ylacetyl]-(S)-2,3-diaminopropionate Trifluoroacetate Salt (Alternative Hydrolysis Procedure)

Methyl $N^2$-(3,5-dimethylisoxazole-4-sulfonyl)-$N^3$-[3-(4-amidinophenyl)isoxazolin-5(R)-ylacetyl]-(S)-2,3-diaminopropionate hydrochloride salt (prepared as in Example 8, Part B, replacing ammonium acetate with ammonium chloride, 1.3 g, 2.6 mmol) was stirred in 6N HCl (150 ml) at room temperature for 20 hours. Solvent was evaporated under reduced pressure to give the crude hydrochloride salt as a white solid (1.1 g, 87%). Purification of 0.17 g crude product by preparative HPLC (Vydac C18 reverse phase column; 2×25 cm; 10 ml/min flow rate; 254 nM; gradient: from 100% $H_2O$ with 0.05% TFA to 20% $H_2O$ and 80% $CH_3CN$ with 0.05% TFA in 50 minutes) yielded 0.12 g (70.6%) of the title compound as a white powder. Chiral HPLC analysis (SFC, Chiralcel OD; 0.46×25 cm; 30° C.; 2.0 ml/min flow rate; 0.1% TFA/22% MeOH/78% $CO_2$; 280 nM; 150 atm) showed >99% d.e. with respect to the (S,S)-diastereomer and >98% chemical purity. MS (ESI): m/e 493 $(M+H)^+$. HRMS (FAB): m/e calculated for $C_{20}H_{25}N_6O_7S$ $(M+H)^+$ 493.150649; Found 493.150544.

UTILITY

The compounds of this invention possess antiplatelet efficacy, as evidenced by their activity in standard platelet aggregation assays or platelet fibrinogen binding assays, as described below. A compound is considered to be active in these assays if it has an $IC_{50}$ value of less than about 1 mM. Platelet aggregation and fibrinogen binding assays which may be used to demonstrate the antiplatelet activity of the compounds of the invention are described below.

Platelet Aggregation Assay:

venous blood was obtained from the arm of a healthy human donor who was drug-free and aspirin-free for at least two weeks prior to blood collection. Blood was collected into 10 mL citrated Vacutainer tubes. The blood was centrifuged for 15 minutes at 150×g at room temperature, and platelet-rich plasma (PRP) was removed. The remaining blood was centrifuged for 15 minutes at 1500×g at room temperature, and platelet-poor plasma (PPP) was removed. Samples were assayed on a aggregometer (PAP-4 Platelet Aggregation Profiler), using PPP as the blank (100% transmittance). 200 pL of PRP was added to each micro test tube, and transmittance was set to 0%. 20 $\mu L$ of various agonists (ADP, collagen, arachidonate, epinephrine, thrombin) were added to each tube, and the aggregation profiles were plotted (% transmittance versus time). The results are expressed as % inhibition of agonist-induced platelet aggregation. For the $IC_{50}$ evaluation, the test compounds were added at various concentrations prior to the activation of the platelets.

Ester prodrugs were preincubated ($10^{-3}$ M F.C.) with 100 IU/ml Porcine liver esterase (Sigma Chemical Co., St. Louis, Mo., #E-3128) for 2 hours at 37° C. Aliquots are then diluted in 0.1M Tris, pH 7.4, to the desired concentrations. Aliquots of 20 $\mu l$ of the esterase pretreated prodrugs are added to 200 $\mu l$ of human platelet rich plasma. Samples were placed in platelet profiler (aggregometer) for 8 minutes at 37° C., followed by the addition of 100 $\mu M$ Adenosine Diphosphate, (Sigma Chemical Co., St. Louis, Mo., #A-6521), to induce platelet aggregation. Platelet aggregation was allowed to proceed for 5 minutes. Percent inhibition is calculated using percent aggregation in the presence of the test compound divided by percent aggregation of control, times 100. This value is subtracted from 100, yielding percent inhibition. Calculation of IC50 is performed on a Texas Instruments TI59 with an IC50 program.

Purified GPIIb/IIIa-Fibrinogen Binding ELISA

The following reagents are used in the GPIIb/IIIa-fibrinogen binding ELISA:

purified GPIIb/IIIa (148.8 $\mu g/mL$);

biotinylated fibrinogen (~1 mg/mL or 3000 nM);

anti-biotin alkaline phosphatase conjugate (Sigma no. A7418);

flat-bottom, high binding, 96-well plates (Costar Cat. no. 3590);

phosphatase substrate (Sigma 104) (40 mg capsules);

bovine serum albumin (BSA) (Sigma no. A3294);

Alkaline Phosphatase buffer–0.1M glycine-HCl, 1 mM $MgCl_2.6H_2O$, 1 mM $ZnCl_2$, pH 10.4;

Binding buffer–20 mM Tris-HCl, 150 mM NaCl, 1 mM $CaCl_2.2H_2O$, 0.02% $NaN_3$, pH 7.0;

Buffer A–50 mM Tris-HCl, 100 mM NaCl, 2 mM $CaCl_2.2H_2O$, 0.02% $NaN_3$, pH 7.4;

Buffer A+3.5% BSA (Blocking buffer);

Buffer A+0.1% BSA (Dilution buffer);

2N NaOH.

The following method steps are used in the GPIIb/IIIa-fibrinogen binding ELISA:

Coat plates with GPIIb/IIIa in Binding buffer (125 ng/100 $\mu L$/well) overnight at 4° C. (Leave first column uncoated for non-specific binding). Cover and freeze plates at −70° C. until used. Thaw plate 1 hour at room temperature or overnight at 4° C. Discard coating solution and wash once with 200 $\mu L$ Binding buffer per well. Block plate 2 hours at room temperature on shaker with 200 $\mu l$ Buffer A+3.5% BSA (Blocking buffer) per well. Discard Blocking buffer and wash once with 200 $\mu L$ Buffer A+0.1% BSA (Dilution buffer) per well. Pipet 11 $\mu L$ of test compound (10× the concentration to be tested in Dilution buffer) into duplicate wells. Pipet 11 $\mu l$ Dilution buffer into non-specific and total binding wells. Add 100 $\mu L$ Biotinylated fibrinogen (1/133 in Dilution buffer, final concentration=20 nM) to each well. Incubate plates for 3 hours at room temperature on a plate shaker. Discard assay solution and wash twice with 300 $\mu L$ Binding buffer per well. Add 100 uL Anti-biotin alkaline phosphatase conjugate (1/1500 in Dilution buffer) to each well. Incubate plates for 1 hour at room temperature on plate shaker. Discard conjugate and wash twice with 300 5l Binding buffer per well. Add 100 $\mu L$ Phosphatase substrate (1.5 mg/ml in Alkaline phosphatase buffer) to each well. Incubate plate at room temperature on shaker until color develops. Stop color development by adding 25 $\mu L$ 2N NaOH per well. Read plate at 405 nm. Blank against non-specific binding (NSB) well. % Inhibition is calculated as 100−(Test Compound Abs/Total Abs)×100.

Platelet-Fibrinogen Binding Assay:

Binding of $^{125}I$-fibrinogen to platelets was performed as described by Bennett et al. (1983) Proc. Natl. Acad. Sci. USA 80: 2417–2422, with some modifications as described below. Human PRP (h-PRP) was applied to a Sepharose column for the purification of platelet fractions. Aliquots of platelets ($5\times10^8$ cells) along with 1 mM calcium chloride were added to removable 96 well plates prior to the activation of the human gel purified platelets (h-GPP). Activation of the human gel purified platelets was achieved using ADP, collagen, arachidonate, epinephrine, and/or thrombin in the presence of the ligand, $^{125}I$-fibrinogen. The $^{125}I$-fibrinogen bound to the activated platelets was separated from the free form by centrifugation and then counted on a gamma counter. For an $IC_{50}$ evaluation, the test compounds were added at various concentrations prior to the activation of the platelets.

The compounds of Formula I of the present invention may also possess thrombolytic efficacy, that is, they are capable of lysing (breaking up) already formed platelet-rich fibrin blood clots, and thus are useful in treating a thrombus formation, as evidenced by their activity in the tests described below. Preferred compounds of the present invention for use in thrombolysis include those compounds having an $IC_{50}$ value (that is, the molar concentration of the compound capable of achieving 50% clot lysis) of less than about 1 $\mu M$, more preferably an $IC_{50}$ value of less than about 0.1 $\mu M$.

Thrombolytic Assay:

Venous blood was obtained from the arm of a healthy human donor who was drug-free and aspirin free for at least two weeks prior to blood collection, and placed into 10 ml citrated Vacutainer tubes. The blood was centrifuged for 15 minutes at 1500×g at room temperature, and platelet rich plasma (PRP) was removed. To the PRP was then added $1 \times 10^{-3}$M of the agonist ADP, epinephrine, collagen, arachidonate, serotonin or thrombin, or a mixture thereof, and the PRP incubated for 30 minutes. The PRP was centrifuged for 12 minutes at 2500×g at room temperature. The supernatant was then poured off, and the platelets remaining in the test tube were resuspended in platelet poor plasma (PPP), which served as a plasminogen source. The suspension was then assayed on a Coulter Counter (Coulter Electronics, Inc., Hialeah, Fla.), to determine the platelet count at the zero time point. After obtaining the zero time point, test compounds were added at various concentrations. Test samples were taken at various time points and the platelets were counted using the Coulter Counter. To determine the percent of lysis, the platelet count at a time point subsequent to the addition of the test compound was subtracted from the platelet count at the zero time point, and the resulting number divided by the platelet count at the zero time point. Multiplying this result by 100 yielded the percentage of clot lysis achieved by the test compound. For the $IC_{50}$ evaluation, the test compounds were added at various concentrations, and the percentage of lysis caused by the test compounds was calculated.

The compounds of Formula I of the present invention are also useful for administration in combination with anti-coagulant agents such as warfarin or heparin, or antiplatelet agents such as aspirin, piroxicam or ticlopidine, or thrombin inhibitors such as boropeptides, hirudin or argatroban, or thrombolytic agents such as tissue plasminogen activator, anistreplase, urokinase or streptokinase, or combinations thereof.

The compounds of Formula I of the present invention may also be useful as antagonists of other integrins such as for example, the $\alpha_v/\beta_3$ or vitronectin receptor, $\alpha_4/\beta_1$ or $\alpha_5/\beta_1$ and as such may also have utility in the treatment and diagnosis of osteoporosis, cancer metastasis, diabetic retinopathy, rheumatoid arthritis, inflammation, and autoimmune disorders. The compounds of Formula I of the present invention may be useful for the treatment or prevention of other diseases which involve cell adhesion processes, including, but not limited to, infammation, bone degradation, rheumatoid arthritis, asthma, allergies, adult respiratory distress syndrome, graft versus host disease, organ transplantation, septic shock, psoriasis, eczema, contact dermatitis, osteoporosis, osteoarthritis, atherosclerosis, metastasis, wound healing, diabetic retinopathy, inflammatory bowel disease and other autoimmune diseases.

Table A below sets forth the antiplatelet activity of representative compounds of the present invention. The indicated compounds were tested for their ability to inhibit platelet aggregation (using platelet rich plasma (PRP)). The $IC_{50}$ value (the concentration of antagonist which inhibits platelet aggregation by 50% relative to a control lacking the antagonist) is shown. In Table A the $IC_{50}$ values are expressed as: +++=$IC_{50}$ of <1 μM; ++=$IC_{50}$ of 1–50 μM; +=$IC_{50}$ of 50–100 μM (μM=micromolar).

TABLE A

| Example | Platelet Aggregation Assay (no esterase) $IC_{50}$ (μM) |
|---|---|
| $N^2$-(3,5-Dimethylisoxazole-4-sulfonyl)-$N^3$-[3-(4-amidinophenyl) isoxazolin-5 (R,S)-ylacetyl]-(S)-2,3-diaminopropionic Acid TFA Salt | +++ |
| $N^2$-(3,5-Dimethylisoxazole-4-sulfonyl)-$N^3$-[3-(4-amidinophenyl) isoxazolin-5 (R)-ylacetyl]-(S)-2,3-diaminopropionic Acid TFA Salt | +++ |
| $N^2$-(3,5-Dimethylisoxazole-4-sulfonyl)-$N^3$-[3-(4-amidinophenyl) isoxazolin-5 (S)-ylacetyl]-(S)-2,3-diaminopropionic Acid TFA Salt | +++ |
| $N^2$-(3,5-Dimethylisoxazole-4-sulfonyl)-$N^3$-[3-(4-amidinophenyl) isoxazolin-5 (R)-ylacetyl]-(S)-2,3-diaminopropionic Acid Methanesulfonate Salt | +++ |

Dosage and Formulation

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an anti-aggregation agent.

The compounds of this invention can be administered by any means that produces contact of the active agent with the agent's site of action, glycoprotein IIb/IIIa (GPIIb/IIIa), in the body of a mammal. They can be administered by any conventional means available for use in conjunction with pharmaceuticals, either as individual therapeutic agents or in a combination of therapeutic agents, such as a second antiplatelet agent such as aspirin or ticlopidine which are agonist-specific. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient,and the effect desired. An ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 0.01 to 10 mg/kg/day. Intravenously, the most preferred doses will range from about 0.001 to about 10 μg/kg/day during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 0.1 milligram to about 50 milligrams of active ingredient per dosage unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules are prepared by filling standard two-piece hard gelatin capsules each with 0.01–100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil is prepared and injected by means of a positive displacement pump into gelatin to form soft gelatin capsules containing 0.01–100 milligrams of the active ingredient. The capsules are washed and dried.

Tablets

A large number of tablets are prepared by conventional procedures so that the dosage unit was 0.01–100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 mL contain 0.01–100 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of the present invention may be administered in combination with a second therapeutic agent selected from: an anti-coagulant agent such as warfarin or heparin; an anti-platelet agent such as aspirin, piroxicam or ticlopidine; a thrombin inhibitor such as a boropeptide thrombin inhibitor, or hirudin; or a thrombolytic agent such as plasminogen activators, such as tissue plasminogen activator, anistreplase, urokinase or streptokinase. The compound of Formula I and such second therapeutic agent can be administered separately or as a physical combination in a single dosage unit, in any dosage form and by various routes of administration, as described above.

The compound of Formula I may be formulated together with the second therapeutic agent in a single dosage unit (that is, combined together in one capsule, tablet, powder, or liquid, etc.). When the compound of Formula I and the second therapeutic agent are not formulated together in a single dosage unit, the compound of Formula I and the second therapeutic agent (anti-coagulant agent, anti-platelet agent, thrombin inhibitor, and/or thrombolytic agent) may be administered essentially at the same time, or in any order; for example the compound of Formula I may be administered first, followed by administration of the second agent (anti-coagulant agent, anti-platelet agent, thrombin inhibitor, and/or thrombolytic agent). When not administered at the same time, preferably the administration of the compound of Formula I and the second therapeutic agent occurs less than about one hour apart.

A preferable route of administration of the compound of Formula I is oral. Although it is preferable that the compound of Formula I and the second therapeutic agent (anti-coagulant agent, anti-platelet agent, thrombin inhibitor, and/or thrombolytic agent) are both administered by the same route (that is, for example, both orally), if desired, they may each be administered by different routes and in different dosage forms (that is, for example, one component of the combination product may be administered orally, and another component may be administered intravenously).

The dosage of the compound of Formula I when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

Although the proper dosage of the compound of Formula I when administered in combination with the second therapeutic agent will be readily ascertainable by a medical practitioner skilled in the art, once armed with the present disclosure, by way of general guidance, where the compounds of this invention are combined with anti-coagulant agents, for example, a daily dosage may be about 0.1 to 100 milligrams of the compound of Formula I and about 1 to 7.5 milligrams of the anti-coagulant, per kilogram of patient body weight. For a tablet dosage form, the novel compounds of this invention generally may be present in an amount of about 0.1 to 10 milligrams per dosage unit, and the anti-coagulant in an amount of about 1 to 5 milligrams per dosage unit.

Where the compounds of Formula I are administered in combination with a second anti-platelet agent, by way of general guidance, typically a daily dosage may be about 0.01 to 25 milligrams of the compound of Formula I and about 50 to 150 milligrams of the additional anti-platelet agent, preferably about 0.1 to 1 milligrams of the compound of Formula I and about 1 to 3 milligrams of antiplatelet agents, per kilogram of patient body weight.

Further, by way of general guidance, where the compounds of Formula I are adminstered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the inhibition of platelet aggregation, the treatment of blood clots, and/or the treatment of thromboembolic disorders, which comprise one or more containers containing a pharmaceutical composition comprising a therapeutically effective amount of a compound of Formula I. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

What is claimed is:

1. A compound of the Formula I:

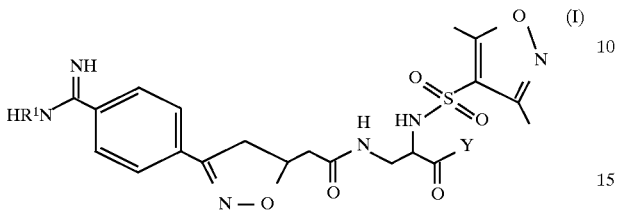

and enantiomeric and diastereomeric forms thereof, and mixtures of enantiomeric and diastereomeric forms thereof, and zwitterion and pharmaceutically acceptable salt forms thereof, wherein:

$R^1$ is hydrogen, $(C_1-C_6)$alkoxycarbonyl, $(C_3-C_7)$ cycloalkoxycarbonyl or aryloxycarbonyl;

Y is selected from the group consisting of:
hydroxy,
$C_1-C_{10}$ alkyloxy,
$C_3-C_{11}$ cycloalkyloxy,
aryl $C_1-C_6$ alkyloxy,
$C_1-C_6$ alkylcarbonyloxy $C_1-C_4$ alkyloxy,
$C_1-C_6$ alkyloxycarbonyloxy $C_1-C_4$ alkyloxy,
$C_3-C_7$ cycloalkylcarbonyloxy $C_1-C_4$ alkyloxy,
$C_3-C_7$ cycloalkyloxycarbonyloxy $C_1-C_4$ alkyloxy,
$C_8-C_{14}$ arylcarbonyloxy $C_1-C_4$ alkyloxy,
$C_1-C_6$ alkyloxy $C_1-C_6$ alkylcarbonyloxy $C_1-C_4$ alkyloxy,
[5-$(C_1-C_6)$alkyl-1,3-dioxa-cyclopenten-2-one-4-yl]methyloxy,
(5-aryl-1,3-dioxa-cyclopenten-2-one-4-yl)methyloxy,
$(C_1-C_4$ alkyl$)_2$N-$(C_1-C_{10})$alkyloxy, or
morpholinoethoxy; and
wherein aryl is phenyl or naphthyl optionally substituted by 1–3 substituents independently selected from methyl, trifluoromethyl, methoxy, amino, dimethylamino, F, Cl, Br and I.

2. A compound of claim 1, and enantiomeric and diastereomeric forms thereof, and mixtures of enantiomeric and diastereomeric forms thereof, and zwitterion and pharmaceutically acceptable salt forms thereof, wherein:

$R^1$ is: H, methoxycarbonyl, ethoxycarbonyl, or benzyloxycarbonyl.

3. A compound of claim 1, and enantiomeric and diastereomeric forms thereof, and mixtures of enantiomeric and diastereomeric forms thereof, and zwitterion and pharmaceutically acceptable salt forms thereof, wherein:

$R^1$ is H; and

Y is selected from the group consisting of:
hydroxy, methoxy, ethoxy, isopropoxy, n-propoxy, n-butoxy, tert-butoxy, iso-butoxy, sec-butoxy, methylcarbonyloxymethoxy, ethylcarbonyloxymethoxy,
t-butylcarbonyloxymethoxy,
cyclohexylcarbonyloxymethoxy,
1-(methylcarbonyloxy)ethoxy,
1-(ethylcarbonyloxy)ethoxy,
1-(t-butylcarbonyloxy)ethoxy,
1-(cyclohexylcarbonyloxy)ethoxy,
i-propyloxycarbonyloxymethoxy,
cyclohexyloxycarbonyloxymethoxy,
t-butyloxycarbonyloxymethoxy,
1-(i-propyloxycarbonyloxy)ethoxy,
1-(cyclohexyloxycarbonyloxy)ethoxy,
1-(t-butyloxycarbonyloxy)ethoxy,
dimethylaminoethoxy, diethylaminoethoxy, (5-methyl-1,3-dioxacyclopenten-2-on-4-yl)methoxy, (5-(t-butyl)-1,3-dioxacyclopenten-2-on-4-yl)methoxy, (1,3-dioxa-5-phenyl-cyclopenten-2-on-4-yl)methoxy, and 1-(2-(2-methoxypropyl)carbonyloxy)ethoxy-.

4. A compound of claim 1, and zwitterion and pharmaceutically acceptable salts forms thereof, and the methyl and ethyl esters thereof, and pharmaceutically acceptable salt forms thereof, selected from:

$N^2$-(3,5-dimethylisoxazole-4-sulfonyl)-$N^3$-[3-(4-amidinophenyl)isoxazolin-5(R)-ylacetyl]-(S)-2,3-diaminopropionic acid;

$N^2$-(3,5-dimethylisoxazole-4-sulfonyl)-$N^3$-[3-(4-amidinophenyl)isoxazolin-5(S)-ylacetyl]-(S)-2,3-diaminopropionic acid;

$N^2$-(3,5-dimethylisoxazole-4-sulfonyl)-$N^3$-[3-(4-amidinophenyl)isoxazolin-5(R)-ylacetyl]-(R)-2,3-diaminopropionic acid; or $N^2$-(3,5-dimethylisoxazole-4-sulfonyl)-$N^3$-[3-(4-amidinophenyl)isoxazolin-5(S)-ylacetyl]-(R)-2,3-diaminopropionic acid.

5. A compound of claim 4 selected from:

$N^2$-(3,5-dimethylisoxazole-4-sulfonyl)-$N^3$-[3-(4-amidinophenyl)isoxazolin-5(R)-ylacetyl]-(S)-2,3-diaminopropionic acid;

$N^2$-(3,5-dimethylisoxazole-4-sulfonyl)-$N^3$-[3-(4-amidinophenyl)isoxazolin-5(R)-ylacetyl]-(S)-2,3-diaminopropionic acid, trifluoroacetic acid salt;

$N^2$-(3,5-dimethylisoxazole-4-sulfonyl-$N^3$[3-(4-amidinophenyl)isoxazolin-5(R)-ylacetyl]-(S)-2,3-diaminopropionic acid, methanesulfonate salt; or $N^2$-(3,5-dimethylisoxazole-4-sulfonyl-$N^3$[3-(4-amidinophenyl)isoxazolin-5(R)-ylacetyl]-(S)-2,3-diaminopropionic acid, hydrochloride salt.

6. A pharmaceutical composition comprising a pharmaceutical carrier and a therapeutically effective amount of a compound of claim 1 or a pharmaceutically acceptable salt form thereof.

7. A pharmaceutical composition comprising a pharmaceutical carrier and a therapeutically effective amount of a compound of claim 2 or a pharmaceutically acceptable salt form thereof.

8. A pharmaceutical composition comprising a pharmaceutical carrier and a therapeutically effective amount of a compound of claim 3 or a pharmaceutically acceptable salt form thereof.

9. A pharmaceutical composition comprising a pharmaceutical carrier and a therapeutically effective amount of a compound of claim 4 or a pharmaceutically acceptable salt form thereof.

10. A pharmaceutical composition comprising a pharmaceutical carrier and a therapeutically effective amount of a compound of claim 5 or a pharmaceutically acceptable salt form thereof.

11. A method of inhibiting the aggregation of blood platelets which comprises administering to a host in need of such inhibition a therapeutically effective amount of a compound of claim 1.

12. A method of inhibiting the aggregation of blood platelets which comprises administering to a host in need of such inhibition a therapeutically effective amount of a compound of claim 2.

13. A method of inhibiting the aggregation of blood platelets which comprises administering to a host in need of such inhibition a therapeutically effective amount of a compound of claim 3.

14. A method of inhibiting the aggregation of blood platelets which comprises administering to a host in need of such inhibition a therapeutically effective amount of a compound of claim 4.

15. A method of inhibiting the aggregation of blood platelets which comprises administering to a host in need of such inhibition a therapeutically effective amount of a compound of claim 5.

16. A method of treating thromboembolic disorders selected from thrombus or embolus formation, harmful platelet aggregation, reocclusion following thrombolysis, reperfusion injury, restenosis, atherosclerosis, stroke, myocardial infarction, and unstable angina, which comprises administering to a host in need of such treatment a therapeutically effective amount of a compound of claim 1.

17. A method of treating thromboembolic disorders selected from thrombus or embolus formation, harmful platelet aggregation, reocclusion following thrombolysis, reperfusion injury, restenosis, atherosclerosis, stroke, myocardial infarction, and unstable angina, which comprises administering to a host in need of such treatment a therapeutically effective amount of a compound of claim 2.

18. A method of treating thromboembolic disorders selected from thrombus or embolus formation, harmful platelet aggregation, reocclusion following thrombolysis, reperfusion injury, restenosis, atherosclerosis, stroke, myocardial infarction, and unstable angina, which comprises administering to a host in need of such treatment a therapeutically effective amount of a compound of claim 3.

19. A method of treating thromboembolic disorders selected from thrombus or embolus formation, harmful platelet aggregation, reocclusion following thrombolysis, reperfusion injury, restenosis, atherosclerosis, stroke, myocardial infarction, and unstable angina, which comprises administering to a host in need of such treatment a therapeutically effective amount of a compound of claim 4.

20. A method of treating thromboembolic disorders selected from thrombus or embolus formation, harmful platelet aggregation, reocclusion following thrombolysis, reperfusion injury, restenosis, atherosclerosis, stroke, myocardial infarction, and unstable angina, which comprises administering to a host in need of such treatment a therapeutically effective amount of a compound of claim 5.

* * * * *